(12) United States Patent
DesNoyer et al.

(10) Patent No.: US 7,365,133 B2
(45) Date of Patent: *Apr. 29, 2008

(54) BLENDS OF POLY(ESTER AMIDE) POLYMERS

(75) Inventors: Jessica Renee DesNoyer, San Jose, CA (US); Stephen Dirk Pacetti, San Jose, CA (US); Lothar Kleiner, Los Altos, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/638,298

(22) Filed: Dec. 12, 2006

(65) Prior Publication Data

US 2007/0093617 A1   Apr. 26, 2007

Related U.S. Application Data

(63) Continuation of application No. 10/960,381, filed on Oct. 6, 2004, now Pat. No. 7,166,680.

(51) Int. Cl.
*A61L 27/34* (2006.01)
*A61L 29/08* (2006.01)
*C08L 77/12* (2006.01)

(52) U.S. Cl. .................. 525/432; 424/423; 525/425; 525/436; 525/437; 525/444; 623/1.15; 623/1.46

(58) Field of Classification Search ............ 525/425, 525/432, 436, 437, 444; 424/423; 623/1.15, 623/1.46

See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,368,090 A | 1/1983 | Mumcu et al. |
| 4,483,975 A | 11/1984 | De Jong et al. |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,386,003 A | 1/1995 | Greene et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,489,667 A | 2/1996 | Knipf et al. |
| 5,516,881 A | 5/1996 | Lee et al. |
| 5,569,463 A | 10/1996 | Helmus et al. |
| 5,578,073 A | 11/1996 | Haimovich et al. |
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |

(Continued)

FOREIGN PATENT DOCUMENTS

DE   196 52 037   6/1998

(Continued)

OTHER PUBLICATIONS

U.S. Appl. No. 10/630,250, filed Jul. 30, 2002, Pacetti et al.

(Continued)

*Primary Examiner*—Ana Woodward
(74) *Attorney, Agent, or Firm*—Squire Sanders & Dempsey LLP

(57) ABSTRACT

Provided herein is a poly(ester amide) (PEA) polymer blend and coatings and medical devices formed of the blend.

5 Claims, No Drawings

U.S. PATENT DOCUMENTS

| | | |
|---|---|---|
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,913 B1 | 8/2001 | Wright et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,316,585 B1 | 11/2001 | Lele et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,383,215 B1 | 5/2002 | Sass |
| 6,387,379 B1 | 5/2002 | Goldberg et al. |
| 6,395,326 B1 | 5/2002 | Castro et al. |
| 6,419,692 B1 | 7/2002 | Yang et al. |
| 6,420,045 B1 | 7/2002 | Faulhammer et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |

| | | |
|---|---|---|
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossainy et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti |
| 6,758,859 B1 | 7/2004 | Dang et al. |
| 6,759,054 B2 | 7/2004 | Chen et al. |
| 6,764,505 B1 | 7/2004 | Hossainy et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwalya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0062147 A1 | 5/2002 | Yang |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091230 A1 | 7/2002 | Hai-Quan et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0166779 A1 | 9/2003 | Kishan et al. |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0106204 A1 | 5/2005 | Hossainy et al. |
| 2005/0112171 A1 | 5/2005 | Tang et al. |
| 2005/0131201 A1 | 6/2005 | Pacetti et al. |
| 2005/0137381 A1 | 6/2005 | Pacetti |
| 2005/0208091 A1 | 9/2005 | Pacetti |
| 2005/0208093 A1 | 9/2005 | Glauser et al. |
| 2005/0245637 A1 | 11/2005 | Hossainy et al. |
| 2005/0265960 A1 | 12/2005 | Pacetti |
| 2005/0271700 A1 | 12/2005 | DesNoyer et al. |
| 2005/0287184 A1 | 12/2005 | Hossainy et al. |

FOREIGN PATENT DOCUMENTS

| | | |
|---|---|---|
| DE | 42 24 401 | 1/1999 |
| EP | 0 301 856 | 2/1989 |
| EP | 0 396 429 | 11/1990 |
| EP | 0 514 406 | 11/1992 |
| EP | 0 583 888 | 2/1994 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

| | | |
|---|---|---|
| GB | 1 137 209 | 12/1968 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/03218 | 1/1998 |
| WO | WO 98/08463 | 3/1998 |
| WO | WO 98/17331 | 4/1998 |
| WO | WO 98/32398 | 7/1998 |
| WO | WO 98/32777 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/56376 | 9/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/26281 | 4/2002 |
| WO | WO 02/34311 | 5/2002 |
| WO | WO 02/56790 | 7/2002 |
| WO | WO 02/58753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017892 | 3/2004 |
| WO | WO 2004/101018 | 11/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/061024 | 7/2005 |
| WO | WO 2005066241 | 7/2005 |

OTHER PUBLICATIONS

U.S. Appl. No. 10/718,278, filed Nov. 19, 2003, Hossainy et al.
U.S. Appl. No. 10/719,516, filed Nov. 21, 2003, Tang et al.
U.S. Appl. No. 10/738,704, filed Dec. 16, 2003, Pacetti et al.
U.S. Appl. No. 10/741,214, filed Dec. 19, 2003, Pacetti et al.
U.S. Appl. No. 10/750,139, filed Dec. 30, 2003, Desnoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 28, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Chung et al., *Inner core segment design for drug delivery control of thermo-responsive polymeric micelles*, Journal of Controlled Release 65:93-103 (2000).
De Lezo et al., *Intracoronary Ultrasound Assessment of Directional Coronary Atherectomy: Immediate and Follow-Up Findings*, JACC vol. 21, No. 2, (1993) pp. 298-307.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Fulton et al., "Thin fluoropolymer films and nanoparticle coatings from the rapid expansion of supercritical carbon dioxide solutions with electrostatic collection", Polymer, vol. 44, No. 13, 2003, pp. 3627-3631.
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Moreno et al., *Macrophage Infiltration Predicts Restenosis After Coronary Intervention in Patients with Unstable Angina*, Circulation, vol. 94, No. 12, (1996) pp. 3098-3102.

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Oikawa et al., *Mechanisms of Acute Gain and Late Lumen Loss After Atherectomy in Different Preintervention Arterial Remodeling Patterns*, The Am. J. of Cardiology, vol. 89, (2002) pp. 505-510.

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Scully et al., *Effect of a heparan sulphate with high affinity for antithrombin III upon inactivation of thrombin and coagulation Factor Xa*, Biochem J. 262, (1989) pp. 651-658.

Shigeno, *Prevention of Cerebrovascular Spasm By Bosentan, Novel Endothelin Receptor*, Chemical Abstract 125:212307 (1996).

van Beusekorn et al., *Coronary stent coatings*, Coronary Artery Disease 5(7):590-596 (Jul. 1994).

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

BLENDS OF POLY(ESTER AMIDE) POLYMERS

CROSS REFERENCE TO RELATED APPLICATION

This is a continuation application of U.S. application Ser. No. 10/960,381, filed on Oct. 6, 2004 now U.S. Pat. No. 7,166,680, the teaching of which is incorporated herein in its entirety.

BACKGROUND OF THE INVENTION

1. Field of the Invention

This invention generally relates to blends of poly(ester amide) (PEA) polymers or copolymers with a low glass transition temperature ($T_g$) and PEA polymers or copolymers with a high $T_g$, which are useful for coating an implantable device such as a drug-delivery stent.

2. Description of the Background

Poly(ester amide) polymers are known for their relatively low glass transition temperatures. For example, co-poly-{[N,N'-sebacoyl-bis-(L-leucine)-1,6-hexylene diester]-[N,N'-sebacoyl-L-lysine benzyl ester]} (PEA-Bz) and co-poly{[N,N'-sebacoyl-bis-(L-leucine)-1,6-hexylene, diester]-[N,N'-sebacoyl-L-lysine 2,2,6,6-tetramethyl-4-amino-1-piperidinyloxyl amide]} (PEA-TEMPO) have a $T_g$ of approximately 23° C. and 33° C., respectively.

Complications related to low $T_g$ manifest themselves as reduced drug release rate control, increased polymer degradation rate, reduced shelf life stability, and potentially increased system mechanical failures. Low $T_g$ materials usually have higher drug permeabilities, which necessitates the use of greater amounts of polymer to control release rate of the drug. Moreover, the low $T_g$ enables the drug to diffuse within the coating. In other words, the drug distribution within a given coating can change with time until an equilibrium state is reached, resulting in release rate shifts. Low $T_g$ materials also tend to be softer, they can be more adhesive to balloons, and are more prone to failure during mechanical perturbations such as crimping and expansion.

The embodiments of the present invention provide for methods addressing these issues.

SUMMARY OF THE INVENTION

Provided herein are polymer blends that include poly(ester amide) (PEA) polymers or copolymers with a low $T_g$ and PEA polymers or copolymers with a high $T_g$. The polymer blends provided herein can form coatings that have improved stability, drug release rate, and mechanical characteristics. The polymer blends can be fine-tuned to have different polymer degradation rates in that, as the effective $T_g$ of the polymer blend is increased, the degradation rate of the polymer blend will decrease.

The PEA polymer blend has an effective $T_g$ equal to or above the $T_g$ of PEA-Bz. In some embodiments, the PEA polymer blend has an effective $T_g$ of about 23° C. or above. The PEA polymer blends described herein can be used to coat an implantable device or to form the implantable device itself, one example of which is a stent. In some embodiments, the PEA polymer blends can be used optionally with a biobeneficial material and/or optionally a bioactive agent to coat an implantable device. In some other embodiments, the PEA polymer blends can be used with one or more biocompatible polymers, which can be biodegradable, bioabsorbable, non-degradable, or non-bioabsorbable polymer.

The implantable device can be a stent that can be a metallic, biodegradable or nondegradable stent. The stent can be intended for neurovasculature, carotid, coronary, puhnonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Provided herein are polymer blends that include poly(ester amide) (PEA) polymers or copolymers with a low $T_g$ and PEA polymers or copolymers with a high $T_g$. The polymer blends provided herein can form coatings that have improved stability, drug release rate, and mechanical characteristics. The polymer blends can be fine-tuned to have different polymer degradation rates in that, as the effective $T_g$ of the polymer blend is increased, the degradation rate of the polymer blend will decrease.

$T_g$ as used herein generally refers to the temperature at which the amorphous domains of a polymer change from a brittle vitreous state to a plastic state at atmospheric pressure. In other words, $T_g$ corresponds to the temperature where the onset of segmental motion in the chains of the polymer occurs, and it is discernible in a heat-capacity-versus-temperature graph for a polymer. When an amorphous or semicrystalline polymer is heated, its coefficient of expansion and heat capacity both increase as the temperature rises, indicating increased molecular motion. As the temperature rises, the polymer's actual molecular volume remains constant. Therefore, a higher coefficient of expansion points to a free volume increase of the system and increased freedom of movement for the molecules. The term "low $T_g$" refers to a $T_g$ of a low $T_g$ material (generally below about 30° C.), e.g., the $T_g$ of PEA-Bz, which has a structure of

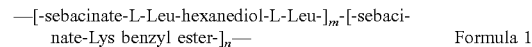

—[-sebacinate-L-Leu-hexanediol-L-Leu-]$_m$-[-sebacinate-Lys benzyl ester-]$_n$—    Formula 1 where m and n are independent positive integers ranging from, e.g., 1 to 100,000.

The PEA polymers forming the blend are substantially mutually soluble in that. one polymer has a solubility of at least about 1 wt %, at least about 5 wt %, at least about 10 wt %, at least about 20 wt %, at least about 50 wt %, at least about 75 wt %, at least about 90 wt %, or at least about 99 wt % in the other polymer and vice versa. In some embodiments, the PEA polymers forming the blend can be substantially thermodynamically miscible, for example, the PEA polymers forming the polymer blend will not phase-separate into microdomains. In some other embodiments, the PEA polymers forming the blend may be mechanically compatible. Mechanically compatible blends are composite systems where the mechanical properties of the blend are not degraded or improved when compared to the individual components that make up the blend as a result of relatively uniform and consistent microphase separation. In contrast, mechanically incompatible blends have degraded mechanical properties when compared to the properties of the individual components as a result of exhibiting gross phase separation. Mechanically incompatible blends typically exhibit low elongation and brittle failure.

The PEA polymer blend has an effective $T_g$ equal to or above the $T_g$ of PEA-Bz. As used herein, the term "effective $T_g$" refers to the $T_g$ of a blend of materials having different $T_g$s. In some embodiments, the PEA polymer blend has an effective $T_g$ of about 23° C. or above. However, raising the effective $T_g$ too high will result in a loss of mechanical integrity, and potentially too low a drug release rate. A preferred range of the effective $T_g$ of the PEA polymer blend is in the range, for example, between about 23° C. and about 75° C. The effective $T_g$ of a thermodynamically compatible polymer blend can be calculated according to the formula $1/T_{g\ mix} = W_1/T_{g1} + W_2/T_{g2}$, where $T_{g\ mix}$ is the glass transition of the blend, while $W_1$, $W_2$, $T_{g1}$ and $T_{g2}$ are the weight fractions and glass transition temperatures of each of the components. For more than 2 components, this equation can be generalized as: $1/T_{g\ mix} = \Sigma W_i/T_{gi}$ where $\Sigma$ represents the summation of i components. Alternatively, the formula is often represented as follows: $T_{g\ mix} = \phi_1 T_{g1} + \phi_2 T_{g2}$, where $\phi$ represents the volume fraction of each component.

The PEA polymer blends described herein can be used to coat an implantable device or to form the implantable device itself, one example of which is a stent. In some embodiments, the PEA polymer blends can be used optionally with a biobeneficial material and/or optionally a bioactive agent to coat an implantable device. In some other embodiments, the PEA polymer blends can be used with one or more biocompatible polymers, which can be biodegradable, bioabsorbable, non-degradable, or non-bioabsorbable polymers.

The implantable device can be a stent that can be metallic, biodegradable or nondegradable. The stent can be intended for neurovasculature, carotid, coronary, pulmonary, aortic, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Modification of Poly(Ester Amide) (PEA) Polymers

In some embodiments, PEA polymers with a high $T_g$ can be formed by modifying a PEA polymer having at least one ester grouping and at least one amide grouping in the backbone that has a low $T_g$. In one embodiment, the low $T_g$ polymer can be a PEA having three building blocks: an amino acid, a diol, and a diacid. The diacid is preferably a C2-C12 diacid, aliphatic or with unsaturation. The amino acid can be, for example, glycine, valine, alanine, proline, glutamine, methionine, leucine, isoleucine, or phenylalanine. An optional second amino acid may be included. The second amino acid can be, for example, lysine, tyrosine, tryptophan, arginine, histidine, glutamic acid, aspartic acid, threonine, serine, or cysteine. The second amino acid may contain a side group to enable the attachment of pharmacologically active compounds or property modifiers. PEA polymers with various thermal properties can be readily prepared by varying these components during synthesis.

Generally, decreasing the polymethylene chain length of the diol or diacid building block will increase the $T_g$. PEA polymers based on amino acids with optical rotation (e.g., L-isomers) will have higher $T_g$s than those based on the corresponding racemic amino acids (D,L-isomers). PEA polymers synthesized from optically active L-amino acids with symmetrical side substituents (e.g., valine, leucine, phenylalanine) will have higher $T_g$s than those synthesized from L-amino acids with nonsymmetrical side substituents (e.g., isoleucine). Amino acids with aromatic substituents (e.g., phenylalanine) tend to have higher $T_g$s.

In one embodiment, the PEA polymer with a low $T_g$ can be PEA-Bz. PEA-Bz can be modified to replace a side group or a backbone group thereof to increase the $T_g$ of the polymer. Some strategies of modifying PEA-Bz to increase $T_g$ are described below.

(1) In PEA-Bz, when the benzyl ester that conjugates to the lysine side group is replaced with TEMPO, the $T_g$ of the resultant PEA polymer, PEA-TEMPO, is increased by 10° C. PEA-TEMPO has a formula of

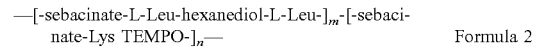

—[-sebacinate-L-Leu-hexanediol-L-Leu-]$_m$-[-sebacinate-Lys TEMPO-]$_n$—    Formula 2

(2) Removing the optional second amino acid (Lys) from PEA-Bz ($T_g$=23° C.), which forms

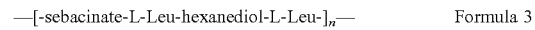

—[-sebacinate-L-Leu-hexanediol-L-Leu-]$_n$—    Formula 3 increases the $T_g$ of the polymer by 14° C.

(3) Decreasing the polymethylene chain length of either the diol or the diacid further increases the $T_g$. For example, the sebacinate in the PEA of formula 3 can be replaced with adipate to form a PEA polymer (Formula 4A) with a $T_g$ of 38° C., the hexanediol in formula 3 is replaced with butanediol to form a PEA polymer (Formula 4B) with a $T_g$ of 47° C., and both the sebacinate or hexanediol in formula 3 can be replaced with adipate and butanediol, respectively, to form a PEA polymer with a $T_g$ of 45° C.:

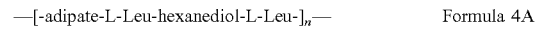

—[-adipate-L-Leu-hexanediol-L-Leu-]$_n$—    Formula 4A

—[-sebacinate-L-Leu-butanediol-L-Leu-]$_n$—    Formula 4B

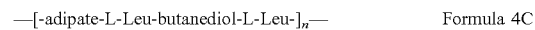

—[-adipate-L-Leu-butanediol-L-Leu-]$_n$—    Formula 4C (4) The effect of optically active amino acids, e.g., an L-isomer, with symmetrical side substituents, which supposedly would result in polymers with higher $T_g$s, depends on the polymethylene chain lengths of the diol and/or diacid. With long chain length diols and diacids, the $T_g$s of the modified PEA polymers are similar to that of the unmodified PEA polymer. For example, the L-leucine of Formula 3 can be replaced with L-valine to form a PEA of Formula 5A with a $T_g$ of 33° C. or L-phenylalanine to form a PEA of Formula 5B with a $T_g$ of 35° C.

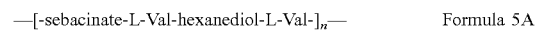

—[-sebacinate-L-Val-hexanediol-L-Val-]$_n$—    Formula 5A

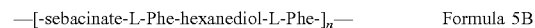

—[-sebacinate-L-Phe-hexanediol-L-Phe-]$_n$—    Formula 5B

With shorter chain length diols and/or diacids, wider variations in $T_g$ can be obtained. For example, the PEA of Formula 4C can be modified by replacing the L-leucine in the formula with L-valine or L-phenylalanine to generate PEAs of Formulae 5C and 5D with $T_g$s of 58° C. and 59° C., respectively. Moreover, the phenylalanine based PEA is semicrystalline, having a melting temperature ($T_m$) of 104° C.

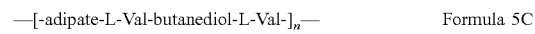

—[-adipate-L-Val-butanediol-L-Val-]$_n$—    Formula 5C

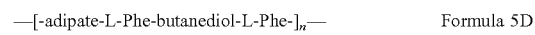

—[-adipate-L-Phe-butanediol-L-Phe-]$_n$—    Formula 5D

In another embodiment, PEA polymers with a high $T_g$ can retain the lysine moiety of the PEA of formulae 1 or 2, using shorter chain length diacids and/or diols. Some examples of these PEA polymers are given below:

—[-adipate-L-Leu-hexanediol-L-Leu-]$_m$-[-adipate-Lys-R]$_n$—R=benzyl ester or TEMPO  Formula 6A —[-sebacinate-L-Leu-butanediol-L-Leu-]$_m$-[-sebacinate-Lys-R]$_n$—R=benzyl ester or TEMPO  Formula 6B —[-adipate-L-Leu-butanediol-L-Leu-]$_m$-[-adipate-Lys-R]$_n$—R=benzyl ester or TEMPO  Formula 6C —[-sebacinate-L-Val-hexanediol-L-Val-]$_m$-[-sebacinate-Lys-R]$_n$—R=benzyl ester or TEMPO  Formula 6D —[-sebacinate-L-Phe-hexanediol-L-Phe-]$_m$-[sebacinate-Lys-R]$_n$—R=benzyl ester or TEMPO  Formula 6E —[-adipate-L-Val-butanediol-L-Val-]$_m$-[-adipate-Lys-R]$_n$—R=benzyl ester or TEMPO  Formula 6F —[-adipate-L-Phe-butanediol-L-Phe-]$_m$-[-adipate-Lys-R]$_n$—R=benzyl ester or TEMPO  Formula 6G The PEA polymers having a first amino acid and optionally a second amino acid can have different ratios of the two amino acids, ranging from, e.g., 1/99 or vice versa. For example, the ratio of the amino acids, lysine and leucine, in PEA polymers of Formulae 1, 2, and 6A-G can range from 1/99 to 99/1, e.g., 1/9, 1/4, 3/7, 2/3, 1/1, 3/2, 7/3, 4/1, or 9/1. The first and the second amino acids can be any of the natural amino acids or unnatural amino acids. Representative natural amino acids can be, for example, valine, leucine, phenylalanine, isoleucine, glycine, glutamic acid, alanine, lysine, tyrosine, methionine, aspartic acid, arginine, serine, threonine, cysteine, asparagine, proline, tryptophan, histidine, and combinations thereof. Representative unnatural amino acids include, but are not limited to, 2-cyclohexylglycine, 2-amino-3,3-dimethyl butyric acid, 2-phenyl glycine, 6-aminocaproic acid, 4-aminobutyric acid, 2-aminoadipic acid, 3-aminobutyric acid, 3-amino-3-phenyl propionic acid, and 1-azetidine-3-carboxylic acid. A compendium of unnatural amino acids may be found in ChemFiles, Unnatural Amino Acids Vol. 2, No. 4 and ChemFiles Unnatural Amino Acids, Vol. 1, No. 5 published by Sigma Aldrich Corporation of St. Louis, Mo.

In a further embodiment, the PEA polymer of formulae 1 or 2 can be modified by conjugating a group other than benzyl ester or TEMPO to the lysine block to increase the $T_g$ of the polymer. For example, a short chain alcohol such as methanol, ethanol or propanol can be used instead of benzyl alcohol, and the resultant PEA polymer is —[-sebacinate-L-Leu-hexanediol-L-Leu-]$_m$-[-sebacinate-Lys R]$_n$—R=methyl, ethyl, or propyl  Formula 7

In general, if a moiety or group smaller than benzyl ester is conjugated to the lysine block, the resultant PEA polymer would have a higher $T_g$ than PEA-Bz. Therefore, the polymer of Formula 7 where R is methyl, ethyl or propyl is expected to have a higher $T_g$ than PEA-Bz.

The PEA polymers described herein can be made by condensation polymerization using, among others, diamino subunits and dicarboxylic acids. The preparation of one example of these PEAs is shown in Scheme I, where the dicarboxylic acid is converted to an active di-p-nitrophenyl derivative.

Scheme I

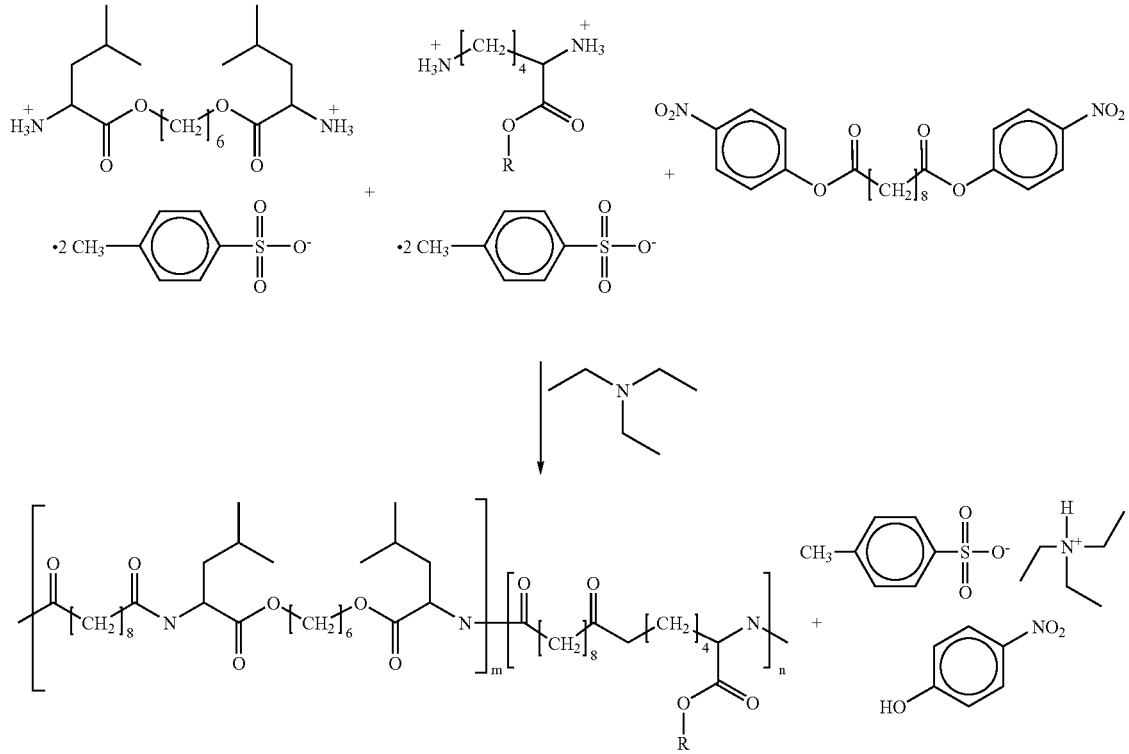

PEA Polymer Blends

In some embodiments, the PEA polymers with a high $T_g$ can be blended with PEA-Bz or PEA-TEMPO. In one embodiment, the PEA with a high $T_g$ does not contain a lysine block. The side group on the lysine block in PEA-Bz or PEA-TEMPO can be conjugated with or attached to another moiety or an active agent.

In another embodiment, the PEA blend can be a blend of a PEA-Bz or PEA-TEMPO having one ratio of lysine to leucine with a second PEA-Bz or PEA-TEMPO having a different ratio of lysine to leucine. One example can be a blend formed of PEA-Bz or PEA-TEMPO having a ratio of 3/1 of the leucine block to lysine block and a PEA-Bz or PEA-TEMPO having a higher ratio of the leucine block to lysine block. A higher ratio of the leucine block to lysine block in PEA-Bz or PEA-TEMPO would increase the $T_g$ of the polymer.

In a further embodiment, the PEA blend can be formed of a PEA polymer having a ratio of 3/1 of the leucine block to the lysine block with a moiety other than benzyl alcohol or TEMPO conjugated to lysine and a PEA polymer of Formulae 1 or 2.

The PEA polymer blend defined above can further include one or more biocompatible polymers, defined below, which are not PEA polymers.

In some other embodiments, the modified PEA polymers and/or PEA-Bz or PEA-TEMPO can be blended with one or more biocompatible polymers, which are not PEA polymers. Because of the desirability of having a $T_g$ above the $T_g$ of PEA-Bz or PEA-TEMPO, as discussed, when the biocompatible polymer is blended with PEA-Bz and/or PEA-TEMPO, the biocompatible polymer would need to have a $T_g$ higher than that of PEA-Bz or PEA-TEMPO and need to be substantially miscible, which is defined above, with the PEA-Bz and/or PEA-TEMPO. The biocompatible polymer is defined below.

Biocompatible Polymer

The biocompatible polymer useful for forming the PEA polymer blend defined herein can be any biocompatible polymer known in the art, which can be biodegradable or nondegradable.

Some representative examples of the biocompatible invention include, but are not limited to, ethylene vinyl alcohol copolymer (commonly known by the generic name EVOH or by the trade name EVAL), poly(hydroxyvalerate), polycaprolactone, poly(lactide-co-glycolide), poly(hydroxybutyrate), poly(hydroxybutyrate-co-valerate), polydioxanone, poly(glycolic acid-co-trimethylene carbonate), polyphosphoester urethane, poly(amino acids), polycyanoacrylates, poly(trimethylene carbonate), poly(iminocarbonate), polyurethanes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as vinylidene fluoride based home or copolymer under the trade name Solefr™ or Kynar™, for example, polyvinylidene fluoride (PVDF) or poly(vinylidene-co-hexafluoropropylene) (PVDF-co-HFP) and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, copolymers of these polymers with poly(ethylene glycol) (PEG), or combinations thereof.

In some embodiments, the biocompatible polymer can be poly(ortho esters), poly(anhydrides), poly(D,L-lactic acid), poly (L-lactic acid), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(trimethylene carbonate), poly(oxaesters), poly(oxaamides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly(ethylene glycol) (PEG), or combinations thereof.

In some other embodiments, the biocompatible polymer can exclude any one or more of the polymers provided above.

The biocompatible polymer can provide a controlled release of a bioactive agent, if included in the coating and/or if binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,581,387 to Labrie, et al.). The release rate of the bioactive agent can be controlled by, for example, selection of a particular type of biocompatible polymer, which can provide a desired release profile of the bioactive agent. The release profile of the bioactive agent can be further controlled by selecting the molecular weight of the biocompatible polymer and/or the ratio of the biocompatible polymer to the bioactive agent. One of ordinary skill in the art can readily select a carrier system using a biocompatible polymer to provide a controlled release of the bioactive agent.

A preferred biocompatible polymer is a polyester, such as one of PLA, PLGA, PGA, PHA, poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), and a combination thereof, and polycaprolactone (PCL).

Bioactive Agents

The PEA polymer blends described herein can form a coating with one or more bioactive agents. These bioactive agents can be any agent which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the polymer blends of the various described embodiments can be formed on an implantable device or prosthesis, e.g., a stent. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Solution blends of PEA-Bz and the PEA of formula 3 can be prepared according to the following procedures. A first composition can be prepared by mixing PEA-Bz and the PEA of formula 3 in a ratio (w/w) of about 1:3 ("PEA-Bz blend"), resulting in an effective $T_g$ of about 32° C. for the PEA-Bz blend, and then adding about 2% (w/w) of the PEA-Bz blend to absolute ethanol. A second composition can be prepared by adding everolimus to the first composition at a drug solid:PEA-Bz blend solution ratio (w/w) of about 1:500, which corresponds to a drug:PEA polymer solids ratio in solution of about 1:10. The above compositions can be agitated to hasten the dissolution process.

Example 2

An everolimus-containing medical article comprised of two layers can be fabricated from the compositions of Example 1 as follows. The second composition of Example 1 is sprayed onto the surface of a bare 12 mm VISION™ stent (Guidant Corp.) and dried to form a coating. An example coating technique comprises spray-coating with a 0.014 fan nozzle, a feed pressure of about 0.2 atm and an atomization pressure of about 1.3 atm; applying about 20 μg of wet coating per pass; drying the coating at about 62° C. for about 10 seconds between passes and baking the coating at about 50° C. for about 1 hour after the final pass to form a dry agent layer. The agent layer can be comprised of about 560 μg of the PEA-Bz blend and about 56 μg of everolimus. A second layer can be applied from the first composition of Example 1 by using the example coating technique. This topcoat layer can contain about 384 μg of the PEA-Bz blend. The total weight of the coating on the stent will be about 1000 μg.

Example 3

Solution blends of PEA-TEMPO and the PEA of formula 4B can be prepared according to the following procedures. A first composition, composition 1, can be prepared by mixing PEA-TEMPO and the PEA of formula 4B in a ratio (w/w) of about 1:1 ("PEA-TEMPO blend 1"), resulting in an effective $T_g$ of about 39° C. for the PEA-TEMPO blend 1, and then adding about 2% (w/w) of the PEA-TEMPO blend 1 to absolute ethanol.

A second composition, composition 2, can be prepared by adding everolimus to the first composition at a solid drug:PEA-TEMPO solution blend ratio (w/w) of about 1:300, which corresponds to a drug:PEA polymer solids ratio in solution of about 1:6. The above compositions can be agitated to hasten the dissolution process.

Example 4

Solution blends of PEA-TEMPO and the PEA of formula 5C can be prepared according to the following procedures. A first composition, composition 3, can be prepared by mixing PEA-TEMPO and the PEA of formula 5C in a ratio (w/w) of about 2:1 ("PEA-TEMPO blend 2"), resulting in an effective $T_g$ of about 39° C. for the PEA-TEMPO blend 2, and then adding about 2% (w/w) of the PEA-TEMPO blend 2 to absolute ethanol.

A second composition, composition 4, can be prepared by adding everolimus to the first composition at a solid drug:PEA-TEMPO solution blend ratio (w/w) of about 1:300, which corresponds to a drug:PEA polymer solids ratio in solution of about 1:6. The above compositions can be agitated to hasten the dissolution process.

Example 5

An everolimus-containing medical article comprised of two layers can be fabricated from the compositions of Examples 3 or 4 as follows. Composition 3 according to Example 3 or composition 4 according to Example 4 can be sprayed onto the surface of a bare 12 mm VISION™ Mstent (Guidant Corp.) and dried to form a coating. An example coating technique includes the step of spray-coating with a 0.014 fan nozzle, a feed pressure of about 0.2 atm and an atomization pressure of about 1.3 atm; applying about 20 μg of wet coating per pass; drying the coating at about 62° C. for about 10 seconds between passes and baking the coating at about 50° C. for about 1 hour after the final pass to form a dry agent layer. The agent layer can be comprised of about 336 μg of either the PEA-TEMPO blend 1 according to Example 3 or the PEA-TEMPO blend 2 according to Example 4 and about 56 μg of everolimus. A second layer can be applied from the composition 1 according to Example 3 or composition 3 according to Example 4 by using the example coating technique. This topcoat layer can contain about 400 μg of either the PEA-TEMPO blend 1 or the PEA-TEMPO blend 2. The two-layer medical article can be formed entirely of PEA-TEMPO blend 1 or PEA-TEMPO blend 2 or combinations thereof. The total weight of the coating on the stent will be about 792 μg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A bioabsorbable implantable device comprising a poly (ester amide) (PEA) polymer blend having a glass transition temperature ($T_g$) above the $T_g$ of poly(ester amide benzyl ester) (PEA-Bz) or poly{[N,N'-sebacoyl-bis-(L-leucine)-1,6-hexylene diester]-[N,N'-sebacoyl-L-lysine 2,2,6,6-tetramethyl-4-amino-1-piperidinyloxyl amide]}(PEA-TEMPO), the PEA polymer blend comprising:

a first PEA polymer having a $T_g$ equal to or below the $T_g$ of PEA-Bz or $T_g$ of PEA-TEMPO, and a second PEA polymer having a $T_g$ above the $T_g$ of PEA-Bz or $T_g$ of PEA-TEMPO.

2. The bioabsorbable implantable device of claim 1, wherein the PEA polymer blend has an effective $T_g$ of equal to or above 37° C.

3. The bioabsorbable implantable device of claim 1, wherein the first PEA polymer or the second PEA polymer comprises unit(s) derived from two amino acids.

4. The bioabsorbable implantable device of claim 1, wherein the PEA polymer blend comprises a PEA polymer of any of formulae 3-7:

| | |
|---|---|
| -[-sebacinate-L-Leu-hexanediol-L-Leu-]$_n$- | Formula 3 |
| -[-adipate-L-Leu-hexanediol-L-Leu-]$_n$- | Formula 4A |
| -[-sebacinate-L-Leu-butanediol-L-Leu-]$_n$- | Formula 4B |
| -[-adipate-L-Leu-butanediol-L-Leu-]$_n$- | Formula 4C |
| -[-sebacinate-L-Val-hexanediol-L-Val-]$_n$- | Formula 5A |
| -[-sebacinate-L-Phe-hexanediol-L-Phe-]$_n$- | Formula 5B |
| -[-adipate-L-Val-butanediol-L-Val-]$_n$- | Formula 5C |
| -[-adipate-L-Phe-butanediol-L-Phe-]$_n$- | Formula 5D |
| -[-adipate-L-Leu-hexanediol-L-Leu-]$_m$-[-adipate-Lys-R]$_n$-R=benzyl ester or TEMPO | Formula 6A |
| -[-sebacinate-L-Leu-butanediol-L-Leu-]$_m$-[-sebacinate-Lys-R]$_n$-R=benzyl ester or TEMPO | Formula 6B |
| -[-adipate-L-Leu-butanediol-L-Leu-]$_m$-[-adipate-Lys-R]$_n$-R=benzyl ester or TEMPO | Formula 6C |
| -[-sebacinate-L-Val-hexanediol-L-Val-]$_m$-[-sebacinate-Lys-R]$_n$-R=benzyl ester or TEMPO | Formula 6D |
| -[-sebacinate-L-Phe-hexanediol-L-Phe-]$_m$-[-sebacinate-Lys-R]$_n$-R=benzyl ester or TEMPO | Formula 6E |
| -[-adipate-L-Val-butanediol-L-Val-]$_m$-[-adipate-Lys-R]$_n$-R=benzyl ester or TEMPO | Formula 6F |
| -[-adipate-L-Phe-butanediol-L-Phe-]$_m$-[-adipate-Lys-R]$_n$-R=benzyl ester or TEMPO | Formula 6G |
| -[-sebacinate-L-Leu-hexanediol-L-Leu-]$_m$-[-sebacinate-Lys R]$_n$-R=methyl, ethyl, or propyl | Formula 7 | wherein m and n are independent positive integers ranging from 1 to 100,000.

5. The bioabsorbable implantable device of claim 1, which is a stent.

* * * * *